(12) United States Patent
Beilfuss et al.

(10) Patent No.: US 9,872,496 B2
(45) Date of Patent: Jan. 23, 2018

(54) MICROBICIDAL PREPARATIONS BASED ON 1, 2-BENZISOTHIAZONLIN-3-ONE WITH A CONTENT OF AROMATIC ALCOHOL

(75) Inventors: Wolfgang Beilfuss, Hamburg (DE); Gisela Hahn, Alveslohe (DE); Klaus Weber, Hamburg (DE); Ralf Gradtke, Tornesch (DE); Wolfgang Siegert, Ellerau (DE)

(73) Assignee: AIR LIQUIDE SANTE (INTERNATIONAL), Paris (FR)

( * ) Notice: Subject to any disclaimer, the term of this patent is extended or adjusted under 35 U.S.C. 154(b) by 1834 days.

(21) Appl. No.: 11/902,401

(22) Filed: Sep. 21, 2007

(65) Prior Publication Data
US 2008/0300283 A1    Dec. 4, 2008

(30) Foreign Application Priority Data
Sep. 21, 2006  (DE) .................. 10 2006 045 066

(51) Int. Cl.
*A01N 25/02* (2006.01)
*A01N 43/80* (2006.01)

(52) U.S. Cl.
CPC .................. *A01N 43/80* (2013.01)

(58) Field of Classification Search
CPC ........ A01N 47/18; A01N 25/02; A01N 59/00; A01N 31/08; A01N 39/00; A61K 31/44255; A61K 8/4926
See application file for complete search history.

(56) References Cited

U.S. PATENT DOCUMENTS

| | | | |
|---|---|---|---|
| 4,871,754 A | | 10/1989 | Bauer et al. |
| 5,160,666 A | * | 11/1992 | Lindner et al. ............... 252/402 |
| 5,762,650 A | * | 6/1998 | Ruggiero et al. ................ 8/490 |
| 6,133,300 A | | 10/2000 | Smith et al. |
| 6,242,391 B1 | | 6/2001 | Fukutani et al. |
| 6,348,483 B1 | * | 2/2002 | Beilfuss et al. .............. 514/374 |
| 2002/0147227 A1 | * | 10/2002 | Exner et al. .................. 514/345 |
| 2004/0151742 A1 | * | 8/2004 | Beilfuss et al. ............. 424/400 |
| 2005/0101487 A1 | | 5/2005 | Beilfuss et al. |

FOREIGN PATENT DOCUMENTS

| | | |
|---|---|---|
| DE | 36 00 271 A1 | 9/1987 |
| DE | 195 48 710 A1 | 6/1997 |
| DE | 102 37 264 A1 | 3/2004 |
| DE | 600 13 468 T2 | 9/2005 |
| DE | 10 2005 045 003 A1 | 4/2007 |
| EP | 0 787 430 A1 | 8/1997 |
| EP | 1 013 751 A1 | 6/2000 |
| EP | 1 767 093 A2 | 3/2007 |
| GB | 2230190 A * 10/1990 ............. A01N 43/80 |
| JP | 57-156405 A | 9/1982 |

OTHER PUBLICATIONS

U.S. Environmental Protection Agency, "Pesticides: Regulating Pesticides: Inert (other) Ingredients in Pesticide Products, List 1-4B," http://www.epa.gov/opprd001/inerts/lists.html (Apr. 30, 2007).

* cited by examiner

*Primary Examiner* — Kyle Purdy
(74) *Attorney, Agent, or Firm* — Young & Thompson

(57) ABSTRACT

Microbicidal preparations containing a) at least one 1,2-benzisothiazolin-3-one or its derivatives; b) at least one 2-mercaptopyridine N-oxide, or its salts and derivatives; c) at least one aromatic alcohol; and d) at least one alkalinizing agent, or a preparation prepared by mixing components a) to d), and having a pH of at least 11, are provided. The microbicidal preparations are clear and storage-stable, and are suitable for use as preservatives.

11 Claims, No Drawings

MICROBICIDAL PREPARATIONS BASED ON 1, 2-BENZISOTHIAZONLIN-3-ONE WITH A CONTENT OF AROMATIC ALCOHOL

FIELD OF THE INVENTION

The present invention relates to microbicidal preparations based on 1,2-benzisothiazolin-3-one.

Preservative preparations which comprise isothiazolin-3-ones (isothiazolone) in combination with derivatives of 2-mercaptopyridine N-oxide (pyrithione below) are known, inter alia, for use as pack preservatives. For example, a combination of 1,2-benzisothiazolone with the zinc salt of 2-mercaptopyridine N-oxide (zinc pyrithione) in water-based emulsions or dispersions is known. However, zinc pyrithione is virtually insoluble in water and organic solvents and therefore cannot be formulated with 1,2-benzisothiazolone to give clear, homogeneous concentrates. Since they have a tendency to form inhomogeneous phases and are difficult to dose, dispersions are preferably not used as pack preservatives.

EP 1 013 751 A1 discloses, in the examples, a water-soluble combination prepared from two components for use as cutting fluid which comprises 1,2-benziso-thiazolone, the sodium salt of 2-mercaptopyridine N-oxide (sodium pyrithione), ethylenediamine, and sodium carbonate and sodium bromide and which is present at a pH of 11.8. Due to the content of ethylenediamine, combinations of this type are burdened with disadvantages. For example, ethylenediamine is comparatively volatile and has an unpleasant odour. Via the gas phase, it leads to a strongly alkaline medium in the surrounding area (i.e. to the risk of corrosion, e.g. for aluminium-containing materials) and can lead to discolorations in preparations. Nitrosamine formation from ethylenediamine derivatives which may form from reactions with further ingredients of microbicidal preparations is not ruled out.

DE 100 40 814 A1 discloses a biocide composition with a content of a pyrithione as biocidal active ingredient which is characterized in that it comprises an iodoalkyl carbamate or a 2-alkylisothiazolin-3-one as a further biocidal active ingredient. Apart from the already described disadvantages of zinc pyrithione preferred according to DE 100 40 814 as pyrithione, the use of 2-n-octylisothiazolone preferred as 2-alkyliso-thiazolone is also associated with disadvantages. 2-n-Octylisothiazolone is virtually water-insoluble and is thus not homogeneously and clearly soluble and distributable in water-containing compositions, which, as mentioned, is required for pack preservatives. Added to this is the fact that it has been found that 2-alkylisothiazolones are of only limited stability in alkaline medium, they are degraded and are then insufficiently microbicidally effective.

DE 195 34 532 describes combinations of 2-n-octyliso-thiazolone with sodium pyrithione and solubility promoters. However, the amount of solubility promoter required when using alkylisothiazolone for preparing a clear solution is undesirably high.

Moreover, preparations are known which comprise formaldehyde or formaldehyde donor compounds. Preparations of this type have high microbicidal effectiveness. Preparations which definitely require the presence of formaldehyde and formaldehyde donor compounds for the microbicidal effect are undesired for certain applications for reasons of toxicity. This is also true for the algicidal triazines, which are prescribed according to DE 102 37 264 A1, which are $N^2$-, $N^4$-, $N^6$-trialkyl-1,3,5-triazines.

SUMMARY OF THE INVENTION

It was an object of the invention to provide preservative preparations which
- are microbicidally effective over a wide pH range, including in particular in the alkaline pH range,
- have a high stability, including a high stability as concentrate, colour stability, low-temperature stability, active ingredient stability at various pH values and temperatures,
- are cost-effective in use,
- are also microbicidally effective in the vapour phase,
- are acceptable for customers, authorities and rating agencies (this requires a low allergy potential) and
- can be formulated as clear concentrates and clear use solutions.

According to the invention, it has now been found that these and other objects are achieved by a preservative preparation which comprises
a) at least one of 1,2-benzisothiazolin-3-one and its derivatives,
b) at least one of 2-mercaptopyridine N-oxide, its salts and derivatives,
c) at least one aromatic alcohol and
d) at least one alkalinizing agent,
where the preparation has a pH of at least 11.

It is clear to the person skilled in the art that components a) to d) prescribed according to the invention can react with one another. For example, it can lead to salt formation of the 2-mercaptopyridine N-oxide and/or of the 1,2-benzisothiazolone with the alkalinizing agent. Accordingly, the invention also provides a preparation which is prepared by mixing components a) to d).

The invention is based, inter alia, on the fact that it has been found that 1,2-benzisothiazolones can be formulated at high pH values and in the presence of aromatic alcohol and 2-mercaptopyridine N-oxide to give clear preparations. In a preferred embodiment, the preparation according to the invention is free from 2-alkylisothiazolones, as are described, for example, in combination with pyrithiones in DE 100 40 814 A1. 2-Alkylisothiazolones are not storage-stable over a long period, particularly at higher pH values, something which is shown in the examples of the present application.

In a further preferred embodiment, the preparation according to the invention is free from formaldehyde and formaldehyde donor compounds which, although highly effective in the gas phase, are toxic and irritate the eyes, the respiratory organs and the skin. Preparations according to the invention are characterized by the fact that they are exceptionally effective even in the absence of formaldehyde and formaldehyde donor compounds.

In a further preferred embodiment, preparations according to the invention are free from algicidal triazines as are known, for example, from DE 102 37 264 in combination with isothiazolones. The use of algicidal triazines is associated with disadvantages because algicidal triazines have virtually no bactericidal or fungicidal effectiveness, they are superfluous in pack preservatives, furthermore they are comparatively expensive and virtually water-insoluble.

DETAILED DESCRIPTION OF THE INVENTION

In a further preferred embodiment, preparations according to the invention are free from quaternary ammonium compounds. Although quaternary ammonium compounds, as known from DE 101 44 187, are exceptionally effective even at high pH values and highly resistant to being washed out, the use of quaternary ammonium compounds is associated with disadvantages because they have a tendency towards foaming and are water-soluble only to a limited extent in strongly alkaline aqueous media. When using the preparation according to the invention, e.g. in household products, quaternary ammonium compounds are incompatible with the anionic surfactants customary therein.

In addition, preparations according to the invention are preferably free from iodopropynylbutyl compounds. Iodopropynylbutyl compounds are very slightly soluble in water, sensitive to hydrolysis and unstable in alkaline medium. They contribute to the (undesired) AOX content of a preparation and have a tendency towards discolorations.

Furthermore, preferred preparations according to the invention are free from the 1,3,5-triazine-2,4,6-tris-alkylaminocarboxylic acid derivatives according to DE 41 38 090 A1. The triazinecarboxylic acid derivatives of DE 41 38 090 are corrosion inhibitors with low bactericidal and fungicidal effectiveness compared to the benzisothiazolone or pyrithione compounds according to the invention. For example, the triazine derivative Becrosan 2126 (a triazine alkanolamide) is insufficiently effective against bacteria and fungi. Substances containing NH groups, such as the triazine carboxylic acid derivatives of DE 41 38 090, can react with nitrite to give nitrosamines. Corrosion inhibitors are not required in the presently claimed compositions (pack preservation).

In a preferred embodiment, the preparation comprises more than 30% by weight of water, preferably more than 50% by weight of water, more preferably 60 to 80% by weight of water, such as, for example, 70% by weight of water. In a further preferred embodiment, the pH of the preparation is at least 12, preferably at least 12.3, more preferably 12.6 to 13.6, in particular 12.8 to 13.3.

a) Benzisothiazolin-3-one

Component a) of the preparations according to the invention is chosen from 1,2-benzisothiazolin-3-one, its derivatives and mixtures thereof. 1,2-Benziso-thiazolone and preferred derivatives are given by the formula:

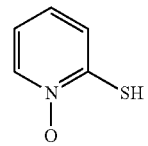

in which R may be H or $C_1$-$C_{10}$-alkyl, $R^1$ may be hydroxy, halogen (in particular chlorine), $C_1$-$C_{10}$-alkyl or $C_1$-$C_{10}$-alkoxy and n can be 0 to 4; if two or more radicals $R^1$ are present, then they can be identical or different. Compounds of this type are disclosed, inter alia, in WO 01/92444 A1. In a preferred embodiment, R is H. Preferred derivatives are halogen-free. A particularly preferred component a) is 1,2-benzisothiazolin-3-one (i.e. n is zero and R is H).

In a preferred embodiment, the amount of component a) is 1 to 20% by weight, preferably 3 to 15% by weight, more preferably 6 to 12% by weight, such as 8 to 10% by weight, for example about 9% by weight.

When calculating the amounts of components a), b) and d) according to the present description of the invention, it should be taken into consideration that 1,2-benzisothiaz-olone and/or 2-mercaptopyridine N-oxide can form salt(s) with the alkalinizing agent in the preparation or can be formulated as salt(s) to give the preparation. Examples of salts of 1,2-benzisothiazolone are alkali metal, alkaline earth metal and amine salts or quaternary ammonium salts, such as Na, K, Li, Ca, Mg, ammonium, 2-hydroxyethylammonium and triethyl-ammonium salts and mixtures thereof. Further examples of such salts are substoichiometric combinations of 1,2-benzisothiazolone and alkalinizing agents (which are reacted with 1,2-benzisothiazolone to give the corresponding salts). Particular preference is given to 1,2-benzisothiazolone, its sodium salt and its potassium salt.

When calculating the amount of 1,2-benzisothiazolin-3-one in the preparation, the amount of alkalinizing agent which has possibly led to salt formation is not taken into consideration, i.e. component a) when calculating the amount is treated as though no salt formation with the alkalinizing agent has taken place. This takes into account the fact that component a) of a preparation according to the invention is usually added as 1,2-benzisothiazolone and not as its salt.

b) 2-Mercaptopyridine N-oxide

As component b) it is possible to use 2-mercapto-pyridine N-oxide with the formula:

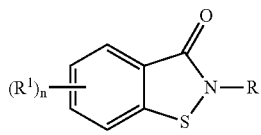

its salts, derivatives (such as 2,2'-dithiobis(pyridine N-oxide), pyrone disulphide) and mixtures thereof. Examples of salts of 2-mercaptopyridine N-oxide are alkali metal, alkaline earth metal and amine salts and quaternary ammonium salts, for example Na, K, Li, Ca, Mg, ammonium, 2-hydroxyethylammonium and triethyl-ammonium salts and mixtures thereof. Preference is given to the sodium salt, which can be used, for example, as a 40% strength aqueous solution.

In a particularly preferred embodiment, component b) is added as salt, for example as sodium pyrithione. Accordingly, if the 2-mercaptopyridine N-oxide in the preparation is in the form of the salt, when stating the amount of component b), this is taken into consideration in as far as only the amount of alkalinizing agent present over and above this salt formation of 2-mercaptopyridine N-oxide is taken into consideration when calculating the amount of the alkalinizing agent component d).

In a preferred embodiment, the amount of component b) in the preparation according to the invention is 1 to 15% by weight, preferably 2 to 11% by weight, more preferably 3 to 9% by weight, such as 4 to 8% by weight, for example 5 to 6% by weight.

In a further preferred embodiment, the weight ratio of component a) to component b) is 1:100 to 100:1, preferably 1:10 to 10:1, in particular 1:2 to 2:1.

c) Aromatic alcohol

Suitable aromatic alcohols are chosen from (i) aryloxyalkanols (glycol monoaryl ethers), (ii) arylalkanols and (iii) oligoalkanol aryl ethers.

(i) Aryloxyalkanols used according to the invention correspond to the formula Ar—O—(CHR)$_n$—OH where R=independently H (when n≥2) or $C_1$- to $C_6$-alkyl, where n is an integer and preferably 2 to 10, more preferably 2 to 6 and in particular 2 or 3. Whereas the group Ar can be a ring-substituted or unsubstituted aryl group, unsubstituted aryl, e.g. phenyl or naphthyl, are preferred. Examples of aryloxyalkanols used according to the invention are phenoxyethanol and phenoxy-propanols. Preferred phenoxypropanols are 1-phenoxy-propanol-2,2-phenoxypropanol-1 or mixtures thereof, and 3-phenoxypropanol-1.

(ii) Arylalkanols used according to the invention have the formula Ar—(CHR)$_n$—OH where R=independently H or $C_1$- to $C_6$-alkyl, where n is an integer and preferably 1 to 10, more preferably 1 to 6 and in particular 1, 2, 3 or 4. While the group Ar may be a ring-substituted or unsubstituted aryl group, unsubstituted aryl, e.g. phenyl or naphthyl, are preferred. Examples of aryl-alkanols are 3-phenylpropanol-1, phenylethyl alcohol, veratryl alcohol (3,4-dimethoxyphenylmethyl alcohol), benzyl alcohol and 2-methyl-1-phenyl-2-propanol. (iii) Oligoalkanol aryl ethers include, for example, phenoxy-di-, -tri- and -oligoethanol and phenoxy-di-, -tri- and -oligopropanol. Besides phenoxyethanol, particularly preferred aromatic alcohols include phenoxypropanols, benzyl alcohol and mixtures thereof.

Preferred preparations according to the invention comprise 1 to 25% by weight, preferably 3 to 20% by weight, more preferably 5 to 15% by weight, such as 7 to 13% by weight, for example about 10% by weight, of component c).

d) Alkalinizing Agent

Examples of alkalinizing agents are alkali metal hydroxides such as NaOH, KOH, LiOH, alkaline earth metal hydroxides, amines, for example alkanolamines, such as ethanolamine, alkali metal carbonates, alkali metal hydrogencarbonates and alkali metal silicates (such as waterglass).

Alkalinizing agents used in preference according to the invention are alkali metal hydroxides, where potassium hydroxide or a mixture of sodium hydroxide and potassium hydroxide are particularly preferred as component d). In one embodiment in which a mixture consisting of sodium hydroxide and potassium hydroxide is used as alkalinizing agent, potassium hydroxide constitutes preferably 20 to 95% by weight of the mixture, more preferably 50 to 90% by weight, in particular 70 to 85% by weight, such as about 80% by weight (accordingly, the fraction of sodium hydroxide in the mixture is 5 to 80% by weight, 10 to 50% by weight, 15 to 30% by weight, such as about 20% by weight).

The amount of component d) in preparations according to the invention is preferably 0.5 to 10% by weight, more preferably 1 to 8% by weight, in particular 2 to 7% by weight, such as 3 to 6% by weight, for example 4 to 5% by weight.

When preparing a preparation according to the invention, it is not absolutely necessary that component d) is added separately, but it is also possible to ensure the high pH of the preparation prescribed according to the invention by introducing alkalinizing agent with component a) and/or component b) by, for example, using a salt of 1,2-benzisothiazolin-3-one, (which is not preferred, but possible) or by using a salt of 2-mercaptopyridine N-oxide (which, in a preferred embodiment, is actually the case, in particular sodium pyrithione).

In one particular embodiment, 2-mercaptopyridine N-oxide is present as alkali metal salt (in particular sodium salt) or is used as such, and equimolar amounts of component a) and component d) are present in the preparation. In a further embodiment which is preferred, a molar excess of alkalinizing agent is present in the preparation (besides alkali metal salt of 2-mercaptopyridine N-oxide, in particular sodium salt), based on the amount of component a). An excess of alkalinizing agent is, in combination with a high pH, a particularly good prerequisite for the formulation of a stable liquid concentrate. Also particularly advantageous is the choice of the alkalinizing agent KOH or a mixture of KOH and NaOH. Phenoxyethanol makes a further contribution to the low-temperature stability and to the microbicidal effectiveness of the gas phase.

In a particularly preferred embodiment, the preparation is prepared from
a) about 9.0% by weight of benzisothiazolone,
b) about 5.6% by weight of 2-mercaptopyridine N-oxide sodium salt,
c) about 10.0% by weight of phenoxyethanol,
d) about 3.6% by weight of potassium hydroxide and about 0.9% by weight of sodium hydroxide and
e) water as the remainder.

This preparation has very good stability in the entire investigated temperature range from −18° C. to +60° C. over at least three months.

The invention is based, inter alia, on the fact that it has been found that 1,2-benzisothiazolones form water-soluble salts with alkali metal hydroxides, whereas 2-alkylisothiazolones, such as 2-n-octylisothiazolone, do not form salts with alkali metal hydroxides, are also virtually water-insoluble in an alkaline medium and, moreover, are unstable.

The preparations according to the invention are characterized by the fact that they have good solubility and distributability in products with a high water content, and a high acceptance by customers and rating agencies. In addition, the components work synergistically together. Furthermore, preparations according to the invention have good storage stability, in particular good low-temperature stability. Moreover, the invention relates to a process for preparing the preparations according to the invention in which component b) (optionally as aqueous dispersion) is initially introduced into water, then component a) is added and then component d) and finally component c).

Moreover, the invention relates to the use of the preparation for preventing or reducing the microbicidal attack of a composition, in particular for the preservation and conservation of water-based products, such as cosmetic or pharmaceutical products, household products or technical products.

In addition, the invention relates to a method of preventing or reducing microbicidal attack of a composition in which the composition (for example a water-based product) is treated with an effective amount of the preparation according to the invention.

Furthermore, the invention relates to a preserved and/or conserved product, for example a water-based product, which comprises the preparation according to the invention.

Examples of further active ingredients which can be used in preparations according to the invention are the preservative active ingredients from Annexe 6 of the Cosmetics Ordinance, alcohols such as ethanol, propanol, polyols or derivatives thereof, for example butylene glycol, pentanediol-1,2, hexanediol-1,2, octanediol-1,2, decanediol-1,2, octoxyglycerol (2-ethylhexyl glycerol ether), octylglycerol, dodecyl-glycerol, glycerol monoesters such as glycerol monolaurate, glycerol caprylate, glycerol caprate, N-acylamino acids or, derivatives thereof, such as N-octanoylglycine, alkali metal sulphite salts, alkali metal bisulphite salts or mixtures of these substances.

Preferred biocidal active ingredients are organohalogen compounds such as bronopol, iodopropynyl butylcarbamate, dibromodicyanobutane, dichlorobenzyl alcohol, chlorofenesin, carboxylic acids or salts thereof such as formic acid, sorbic acid, salicylic acid, benzoic acid, dehydracetic acid, undecylenic acid, phenols such as parabens or salts thereof (e.g. methyl-, ethyl-, propyl- and butylparaben), o-phenylphenol, p-chloro-m-cresol, aldehydes such as formaldehyde, glutardialdehyde, succinaldehyde, aldehyde donor compounds such as formaldehyde donor compounds (e.g. O- or N-formals such as ethylene glycol bishemiformal, benzyl alcohol bishemiformal, Grotan BK, Grotan OX, Grotan OF, Grotan OK, tetramethylol-acetylenediurea, dimethyloldimethylhydantoin, diazolidinylurea, dimethylolurea), succinaldehyde donor compounds (e.g. dimethoxytetrahydrofuran), glutar-dialdehyde donor compounds (e.g. alkoxydihydropyrans, alkoxytetrahydropyrans), isothiazolones such as methyl-, chloromethyl-, octylisothiazolone, cationic compounds and quaternary ammonium compounds such as benzalkonium chloride, benzethonium chloride, Vantocil IB, Bardac 22, chlorhexidine salts, alexidine salts, peroxides such as $H_2O_2$, methyl ethyl ketone peroxide, t-butyl hydroperoxide, peracetic acid or mixtures thereof.

Examples of functional additives are complexing agents such as EDTA, NTA, pH correctors or buffers such as citrates, phosphates, antioxidants such as vitamin E, phenol derivatives, low-temperature stabilizers such as glycols, glycol ethers, solubility promoters such as alcohols, glycols, glycol ethers, e.g. ethylene glycol, triethylene glycol, 1,2-propylene glycol, crystallization preventors, viscosity modifiers, thickeners or salts thereof or mixtures of these substances.

The advantages of the invention are particularly evident from the following examples.

EXAMPLE 1

Decomposition of 2-n-octylisothiazolone at a pH of about 13

1.1% by weight of Kathon 893F (2-n-octylisothiazolone, 45% strength in glycol), 48.89% by weight of methanol and 50% by weight of sodium hydroxide solution (c=0.5 mol/l) were used to prepare a mixture with a pH of about 13 whose active ingredient content (in % by wt.) was monitored using HPLC over a period of 35 days. Storage took place at 20° C. The results are shown below.

| Days | 2-n-Octylisothiazolone |
|---|---|
| 0 | 0.53 |
| 2 | 0.43 |
| 4 | 0.36 |
| 7 | 0.29 |
| 11 | 0.23 |
| 21 | 0.13 |
| 35 | 0.07 |

This shows that 2-alkylisothiazolones, such as 2-n-octylisothiazolone, are not stable under alkaline conditions.

EXAMPLE 2

The following preparations were prepared by mixing the stated components. The quantitative data in the table refer to the amounts of active constituent. 2-Mercapto-pyridine N-oxide was used as the sodium salt sodium pyrithione (40% strength aqueous solution), 1,2-benzisothiazolinone was used as 85% strength hydrous solid. Potassium hydroxide and sodium hydroxide were in each case used as 45% strength aqueous solution.

|  | I | II (comparison) | III | IV (comparison) |
|---|---|---|---|---|
| Sodium pyrithione | 5.6 | 5.6 | 5.6 | 5.6 |
| 1,2-Benzisothiazolin-3-one | 9.0 | 9.0 | 9.0 | 9.0 |
| Potassium hydroxide | 3.6 | — | 4.5 | — |
| Sodium hydroxide | 0.9 | 4.5 | — | — |
| Phenoxyethanol | 10.0 | — | 10.0 | 10.0 |
| Water | ad 100 | ad 100 | ad 100 | ad 100 |
| Solubility | Dissolved after 10 min | Not dissolved | Dissolved after 10 min | Not dissolved |
| Appearance after preparing the preparation | Clear, brownish-yellow solution | 2 phases; a lot of white sediment, above yellow-orange solution with white flocks | Clear, brownish-yellow solution | Cloudy, yellowish solution with a lot of sediment |
| Gardner colour number after preparation | 3.9 |  | 4 |  |
| pH (pH paper) after preparation | 13-14 | 13-14 | 13-14 | 8-9 |
| Appearance after storage for 2 days at −5° C. | Without change | Without change | Without change | Without change |
| Appearance after storage for 2 days at +4° C. | Without change |  | Without change |  |
| Appearance after storage for 2 days at 25° C. | Without change |  | Without change |  |

Comparison preparation II shows that, particularly at a high content of sodium pyrithione and 1,2-benzisothiazolone, a high pH on its own does not automatically produce clear preparations with low-temperature stability. The results with comparison preparation IV show that the presence of the aromatic alcohol phenoxyethanol on its own is likewise not an adequate condition for producing a clear preparation with low-temperature stability. The preparations I and III according to the invention with both a high pH and also a content of aromatic alcohol demonstrate that through the formulation of preparations according to the invention the problems of (i) solubility and (ii) (low-temperature) stability are overcome.

The invention claimed is:

1. A preservative preparation, consisting of:
   (a) 6 to 12% by weight of 1,2-benzisothiazolin-3-one;
   (b) 3 to 9% by weight of 2-mercaptopyridine N-oxide or a salt thereof;
   (c) 5 to 15% by weight of at least one aromatic alcohol, the alcohol selected from the group consisting of phenoxyethanol, phenoxypropanol, benzyl alcohol and mixtures thereof;
   (d) 2 to 7% by weight of at least one alkalinizing agent comprising potassium hydroxide or a mixture of potassium hydroxide and sodium hydroxide; and
   (e) 60 to 80% by weight of water,
   wherein the preparation has a pH of at least 11, and is free of algicidal triazines.

2. The preparation according to claim 1, consisting of:
   (a) 8 to 10% by weight of 1,2-benzisothiazolin-3-one;
   (b) 4 to 8% by weight of 2-mercaptopyridine N-oxide or a salt thereof;
   (c) 7 to 13% by weight of the at least one aromatic alcohol; and
   (d) 3 to 6% by weight of at least one alkalinizing agent comprising potassium hydroxide or a mixture of potassium hydroxide and sodium hydroxide.

3. The preparation according to claim 1, wherein the water in present in an amount of at least 70% by weight.

4. The preparation according to claim 1, having a pH of at least 12.

5. The preparation according to claim 1, wherein the salt of 2-mercapto-pyridine N-oxide is a sodium salt, an alkali metal, an alkaline earth metal or a zinc salt.

6. A process for preparing the preparation according to claim 1, comprising:
   (1) first, adding component b) to water, then
   (2) adding component a), then
   (3) adding component d), and finally
   (4) adding component c).

7. The preparation according to claim 1, having a pH in a range of 12.8 to 13.3.

8. The preparation according to claim 1, wherein component (a) is present in an amount of 8% to 10% by weight.

9. The preparation according to claim 1, wherein component (b) is present in an amount of 4% to 8% by weight.

10. The preparation according to claim 1, wherein component (c) is present in an amount of 7% to 13% by weight.

11. The preparation according to claim 1, wherein the at least one alkalizing agent (d) consists of a mixture of sodium hydroxide and potassium hydroxide, said mixture having at least 70% potassium hydroxide by weight.

* * * * *